US006617319B2

(12) United States Patent
Gonsalves et al.

(10) Patent No.: US 6,617,319 B2
(45) Date of Patent: Sep. 9, 2003

(54) METHODS OF USE FOR 2-DEOXY ECDYSTERONE (75) Inventors: Cynthia Olimpia Lydia Gonsalves, Goa (IN); Perunninakulath Parameswaran Subrayan, Goa (IN); Chandrakant Govind Naik, Goa (IN); Chittur Thelakkat Achuthankutty, Goa (IN)

(73) Assignee: Council of Science and Industrial Research, New Delhi (IN)

( * ) Notice: Subject to any disclaimer, the term of this patent is extended or adjusted under 35 U.S.C. 154(b) by 0 days.

(21) Appl. No.: 10/050,616

(22) Filed: Jan. 16, 2002

(65) Prior Publication Data

US 2002/0147355 A1 Oct. 10, 2002

Related U.S. Application Data (62) Division of application No. 09/531,744, filed on Mar. 21, 2000, now abandoned.
(51) Int. Cl.[7] ................................................ A61K 31/56
(52) U.S. Cl. ...................... 514/182; 514/169; 514/170; 514/171; 514/181; 514/182
(58) Field of Search ................................. 552/542, 545, 552/526; 514/182, 181, 171, 170, 169

(56) References Cited

PUBLICATIONS

Bathori et al., "Droplet counter–cuurent chromatography to isolate ecdysteroids from the herbs of Silene tatarica (L.) Pers", Acta Pharm. Hung., vol. 66 (3), pp. 125–131, (1996), AN 1996:448935, abstract only, American Chemical Society.

Sturaro et al. "A new, unexpected marine source of a molting hormone, Isolation of ecdysterone in large amounts from the zoanthid *Gerardia savaglia*", Experientia, vol. 38, pp. 1184–1185, (1982), Birkhauser Verlag.

Bossmar et al. "Recpetors for and Myometrial Responses to Oxytocin and Vasopressin in Preterm and Term Human Pregnancy: Effects of the Oxytocin Antagonist Atosiban", Am. J. Obster. Gynecol., vol. 171(6), pp. 1634–41 (1994), Mosby–Year Books, Inc.

(List continued on next page.)

Primary Examiner—Sabiha Qazi
(74) Attorney, Agent, or Firm—Ohlandt, Greeley, Ruggiero & Perle, L.L.P.

(57) ABSTRACT

The invention provides a process for the isolation of 2-deoxy ecdysterone from Zoanthus sp process comprising the steps (a) preparing crude methanol extract of Zoanthus sp., (b) subjecting the crude methanol extract to fractionation using petroleum ether, ethyl acetate, chloroform, n-butanol and mixtures thereof to yield a fraction, (c) subjecting the active fraction to flash chromatography over silica gel to obtain partially purified active compound, and (d) subjecting the active subfraction obtained from step (c) above to gel permeation chromatography to obtain the active pure compound.

13 Claims, 6 Drawing Sheets

OTHER PUBLICATIONS

Castro et al. "Plasma Levels of Atrial Natriuretic Pepetide in Normal and Hypertensive Pregnancies: A Meta–Analysis", Am. J. Obstet. Gynecol., vol. 171(6), title pg., pp. 1A & 2A & pp. 1642–1651, (1994), Mosby–Year Books, Inc.

Tighe–Ford, D. J., "Hormonal Aspects of Barnacle Antifouling Research", Marine Natural Products Chemistry, pp. 383–402, (1977), Plenum Press.

Quinn, R. J., "Chemistry of Aqueous Marine Extracts Isloation Techniques", Bioorganic Marine Chemistry, vol. 2, pp. 25–27, (1988).

Rao et al., "Alkaloids from a Marine Zoanthid", J. Org. Chem., vol. 50, pp. 3757–60, (1985), American Chemical Society.

Moore et al., "Palytoxin: A New Marine Toxin from a Coelenterate", Science, vol. 172 (3982), title page & pp. 495–498, (1971), American Association for the Advancement of Science.

Buchanan et al., "Cervical Ripening with Prostaglandin $E_2$ Vaginal Suppositories", Obstetrics & Gynecology, vol. 63 (5), pp. 659–663, The American College of Obstetricians and Gynecologists.

Thomas Bossmar and Jazec Szamatowicz, *Receptors for and Myometrial Responses to Oxytocin and Vasopressin in Preterm and Term Human Pregnancy: Effects of the Oxylocin Antagonist Atosiban*, Am. J. Obstet. Gynecol., pp. 1634–1641 (1994).

Lony C. Castro, Clavin J. Hobel and Jeffrey Gornbein, *Plasma Levels of Atrial Natriuretic Pepetide in Normal and Hypertensive Pregnancies: A Meta–Analysis,* Am. J. Obstet. Gynecol., vol. 171, No. 6, title pg., pp. 1A & 2A & pp. 1642–1651 (Dec. 1994).

Tige–Ford, D. J., *Hormonal Aspects of Barnacle Antifouling Research,* Marine Natural Products Chemistry, pp. 383–402, (1977).

Quinn, R. J., *4.7.3 Other Coelenterates,* Bioorganic Marine Chemistry, vol. 2, pp. 25–27 (1988).

C. Bheemasankara Rao, Ammanamanchi S. R. Anjaneyulu, Nittala S. Sarma and Yenamandra Venkateswarlu, *Alkaloids from a Marine Zoanthid*, J. Org. Chem., vol. 50, pp. 3757–60, (1985).

Richard E. Moore and Paul J. Scheuer, *Palytoxin: A New Marine Toxin from a Coelenterate*, publication Science, vol. 172, No. (3982), title page & pp. 495–498, (Apr. 1971).

Dennis Buchanan, James Macer and Margaret L. Yonekura, *Cervical Ripening with Prostaglandin $E_2$ Vaginal Suppositories*, Obstetrics & Gynecology, vol. 63, No. 5, ©1984 by The American College of Obstetricians and Gynecologists, pp. 659–663 (May 1984).

2 - deoxy ecdysterone

METHODS OF USE FOR 2-DEOXY ECDYSTERONE

This a divisional application of application Ser. No. 09/531,744, filed Mar. 21, 2000 now abandoned; the disclosure of which is incorporated herein by reference.

FIELD

The present invention relates to a process for the isolation of 2-deoxy ecdysterone from Zoanthus sp useful as an oxytocic agent. The invention also relates to a method of inducing uterus contractions in mammals by administering an effective amount of 2-deoxy ecdysterone obtained from Zoanthus sp.

BACKGROUND

The animal Zoanthus sp is a marine invertebrate belonging to the Phylum Coelenterata, class Anthozoa and order Zoanthidea. Several bioactive compounds have been isolated from this source. Most important among them is the highly toxic palytoxin ($LD_{50}$ in mice=0.15 mg/Kg, Moore R E and Scheuer P J, 1971, *Science*, 172:495), which is also an active cardiovascular agent. Other compounds reported from this group of animals are: homopalytoxin, bishomopalytoxin, neopalytoxin, deoxypalytoxin (Quinn R. J in *Bioorganic Marine Chemistry*, Vol 2, 1988, Edited by P J Scheuer, pp 25–27), two pyrazine derivatives: palythazine and isopalythazine, and a group of nitrogen pigments, paragracine I–VII (Bakus G J, Targett N M and Schulte B, 1986 ,*J Chem Ecol*, Vol 12:951–987), 3-norpseudozoanthoxanthin (Cimino G, De Stefano S, Fenical W, Lin G H Y, Wing R M, Radick P and Sima J J, *J Am Chem Soc*, 1973, 95:4049) besides the alkaloids, zoanthamine, zoanthenamine and zoanthamide (Rao C B, Anjaneyulu A S R, Sarma N S, Venkateswarlu Y, Rosser R M, Faulkner D J, 1985. *J Org Chem*, 50:3757–3760).

Ecdysones and ecdysterones are moulting hormones found in crustaceans and insects (D J Tighe-Ford, 1977. Hormonal aspects of Barnacle antifouling research. In *Marine Natural Products Chemistry*, D J Faulkner and W H Fenical (eds), Plenum Press, 383). The zoanthid *Gerardia savaglia* was found to contain large quantities of the crustacean molting hormone, ecdysterone (Sturaro A, Guerriero A, De Clauser R and Pietra F, *Experientia*, 1982, 38:1184–1185). The related compounds, Palythoalones A and B (ecdysteroids) from the marine zoanthid *Palythoa australiae* have recently been isolated. (Shigemori H; Sato Y; Kagata T; Kobayashi J, 1999. Palythoalones A and B, new ecdysteroids from the marine zoanthid *Palythoa australiae*. *J. Nat. Prods*, 62(2):373).

Agents that stimulate the pregnant uterus and are of importance in obstetrics are:

1-Oxytocics: Oxytocin and ergometrine
2-Prostaglandin E and F type compounds

Oxytocin causes regular coordinated uterine contractions each followed by relaxation. It is the drug of choice used to induce or augment labour when the uterine muscle is not functioning adequately (Rang H. P., Dale M. M; Ritter J. M., Pharmacology, third edition, pp 470, Churchill Livingstone, 1995). It is particularly used in those cases such as diabetes, isoimmunisation, hypertensive states, intrauterine growth retardation, placental insufficiency in which continuation of pregnancy is considered to be more harmful to the mother and/or foetus than the risks of delivery or pharmacological induction (Andrew J. Nichols; Robert R. Ruffolo, Jr., Uterine Pharmacology, in Principles of Pharmacology. Basic Concepts and Clinical Applications. Ed. Paul L. Munson. pp 202, 1995). Oxytocin may also be used in the treatment of postpartum hemorrhage resulting from uterine atony (Andrew J. Nichols; Robert R. Ruffolo, Jr., Uterine Pharmacology, in Principles of Pharmacology. Basic Concepts and Clinical Applications. Ed. Paul L. Munson. pp 202, 1995). Historically the ergot alkaloids were the first agents used to initiate or accelerate parturition. In modern obstetrics, oxytocin is used for this function and ergot alkaloids are most often used for treatment of postpartum hemorrhage (Cornelia R. Graves, Agents that cause contraction or relaxation of the uterus, in Goodman and Gilman's, The Pharmacological basis of therapeutics. Eds. Perry B. Molinoff and Raymond W. Ruddon, pp. 939, 1996). Specific receptors for oxytocin in human myometrium have been identified and differences in receptor density at various stages of labour also have been noted (Bossmar T; Akerlund M; Fantoni G; Szamatowicz J; Melin P; and Maggi M., Receptors for and myometrial responses to oxytocin and vasopressin in preterm and term human pregnancy: effects of the oxytocin antagonist atosiban. Am. J. Obstet. Gynecol. 1994, 171: 1634–1642, 1994). Oxytocin has dual effects on the uterus. It regulates the contractile properties of myometrial cells and elicits prostaglandin production by endometrial/decidual cells.

Prostaglandins currently used in obstetrical practice include $PGE_2$, $PGF_{2\alpha}$ and the synthetic derivative 15-methyl $PGF_{2\alpha}$. More recently, the $PGE_1$ analog, misoprostol, has been under clinical investigation for use as an abortifacient and cervical ripening.

The major use of $PGE_2$ (dinoprostone, Prostin $E_2$) and 15-methyl $PGF_{2\alpha}$ (Carboprost, Hemabate) currently approved in the U.S.A is for the performance of mid-trimester abortions. 15-Methyl $PGF_{2\alpha}$ is also used as an alternative to ergonovine or oxytocin in the treatment of postpartum hemorrhage. In addition, numerous studies have supported the beneficial effect of locally applied $PGE_2$ as a cervical ripening agent (Buchanam D; Macer J and Yonekura M. L., Cervical Ripening with Prostaglandin $E_2$ Vaginal Suppositories. Obstet. Gynecol. 1984, 63:659–663).

Prostaglandins $E_2$ and $F_2\alpha$, presently used for clinical purposes are not very stable. For example, radiolabelled $PGE_2$, when injected into human volunteers, about 50% of the radioactivity is excreted in the urine within 5 hours. The corresponding value for $PGF_{2\alpha}$ is around 90% (W P Collins; E A Willman, 1978. Prostaglandins and uterine functions, In Topics in hormone chemistry, W R Butt (eds), Ellis Horwood Publishers, 183). At least 15 compounds have been identified in both the studies by mass spectrometry.

OBJECTS

The main objective of the present investigation is to provide a process for the isolation of 2-deoxy ecdysterone from Zoanthus sp.

Another objective of the investigation is to find out the unknown property of the compound, 2-deoxy ecdysterone, isolated and purified from Zoanthus sp in inducing uterus contractions.

Still another objective of the invention relates to a method of inducing uterus contractions in mammals, said method comprising administering in known manner an effective amount of 2-deoxy ecdysterone which isolated and purified from Zoanthus sp.

Yet another objective of the invention is to provide a stable bioactive compound which may be useful in obstetrics, to induce or augment labour, to control postpartum uterine atony and hemorrhage, to cause uterine contraction after cesarean section or during uterine surgery or to induce therapeutic abortion.

DETAILED DESCRIPTION

The present investigation undertaken by the inventors has led to the development and standardization of a facile method for the isolation and purification of 2-deoxy ecdysterone from a new source, Zoanthus sp using flash chromatography over silica gel and gel permeation chromatography over Sephadex LH-20. The invention further provides a novel biomedical use of this compound as a potent oxytocic agent. The invention has established that this compound is more potent than the standard oxytocin and $PGF_{2\alpha}$ at the concentration of 200 µg/ml. The compound, 2-deoxy ecdysterone is also very stable and soluble in aqueous solvents and may have wider therapeutical applications.

The compound, 2-deoxy ecdysterone also known as 2-deoxy β-ecdysone or 2-deoxy-20-hydroxy ecdysone, was found to be effective in inducing contractions in the guinea pig uterus. It was found that the percentage of active component oxytocin contained in 50 µg/ml of compound amounts to 80.8%, that at 100 µg/ml to 92.3% which further increases to 118.0% at concentration of 200 µg/ml. Uterine contractions produced by the compound were also compared with the standard contraction produced by prostaglandin ($PGF_{2\alpha}$). It was observed that for the active compound, the percentage of active component $PGF_{2\alpha}$ contained in 50 µg/ml of compound amounts to 69.4%, that at 100 µg/ml to 82.3% which further increases to 114.1% at concentration of 200 µg/ml. Possible use of the compound in obstetrics could be to induce or augment labour, to control post partum uterine atony and hemorrhage, to cause uterine contraction after cesarean section or during uterine surgery or to induce therapeutic abortion.

BRIEF DESCRIPTION OF ACCOMPANYING DRAWINGS

In the drawing accompanying this specification.

In the accompanying

In the accompanying

In the accompanying

In the drawing accompanying

In the drawing accompanying

Accordingly, the present invention provides a process for the isolation of 2-deoxy ecdysterone from Zoanthus sp, said process comprising the steps of:

i) Preparing the crude methanol extract of the Zoanthus sp by conventional methods, ii) Subjecting the crude methanol extract to fractionation using petroleum ether, ethyl acetate, n-butanol to yield the respective fractions, iii) Subjecting the active chloroform fraction to flash chromatography over silica gel (60–120 mesh) using gradient acetone-petroleum ether (30:70 to 100:0) as eluant to obtain partially purified active compound, and iv) Subjecting the active subfraction obtained from step (c) above to gel permeation chromatography over Sephadex LH-20 using acetone as eluant to obtain the active pure compound.

In an embodiment the active pure compound is identified as 2-deoxy ecdysterone from its IR, $^1H$ NMR, $^{13}C$ NMR and mass spectral data.

In another embodiment the compound 2-deoxy ecdysterone is active upto 80.8, 92.3 and 118.0% at concentrations of 50, 100 and 200 µg/ml respectively as compared to standard oxytocin.

In yet another embodiment the compound 2-deoxy ecdysterone is active upto 69.4, 82.3 and 114.1% at concentrations of 50, 100 and 200 µg/ml respectively as compared to standard $PGF_{2\alpha}$.

In still another embodiment the compound may have the following potential uses in obstetrics: to induce or augment labour, to control postpartum uterine atony and hemorrhage, to cause uterine contraction after cesarean section or during uterine surgery or to induce therapeutic abortion.

The invention is further explained with the help of the following examples and should not be construed to limit the scope of the invention.

EXAMPLE I

Zoanthus sp collected from Anjuna beach (Goa) was used for the invention. The animals were carefully scrapped from the intertidal rocks during the low tide period using a metal spatula. About 2 kg wet weight of the specimens were used for the study. The specimens were thoroughly washed with fresh sea water and soaked in methanol for one week for crude extract preparation. Extracts were obtained from the whole body tissue. The solvent extract was decanted, filtered through Whatman filter paper I and vacuum evaporated at 40° C. to concentrate to crude extract. About 30 gm of crude extract was thus obtained. This example illustrates the methodology used for preparation of the crude methanol extract from Zoanthus sp.

EXAMPLE II

A female virgin guinea pig that was in oestrous and weighing around 400–500 gm was used for the test. The animal was killed by a stunning blow on the head. The abdomen was immediately cut open. The uterus was dissected out and placed in a petri plate containing aerated De Jalon's solution (M. N Ghosh, in fundamentals of Experimental Pharmacology, 1984, second edition, Scientific book agency, Calcutta). The uterus was freed from fat and the two uterine horns were separated by cutting the lower end. Only one horn was used for the experiment. Two small loops of thread were made at each end of the uterus and kept in a tissue bath of 10 ml capacity containing aerated De Jalon's solution. The lower end was tied to the tissue holder and the upper end to the writing lever. The lever was balanced to provide a tension of 1 g with plasticene. The tissue was left in the bath for ½ hr for stabilisation before starting the experiment and the physiological solution (De Jalon's solution) was renewed every 10 minutes. This example illustrates the procedure used for the preparation of the guinea pig uterus for testing the oxytocic property of the pure white solid, 2-deoxy ecdysterone.

EXAMPLE III

After stabilisation, 2–3 doses of oxytocin (Parke Davis Ltd, Hyderabad) were added as standard to the physiological solution, the dose depending on the amplitude of contraction to obtain uniform contractions. The extract was then added to the bath (50 & 250 µg/ml) and allowed to act for one minute. If a contraction was observed during that one-minute period, extract was considered to be oxytocin-like and having oxytocic property. After every contraction, the tissue was immediately washed twice with the physiological solution and relaxed for 10 minutes. The same procedure was followed for the crude extract, fractions and the purified white solid, identified as 2-deoxy ecdysterone.

The oxytocic activity of the crude, fractions and the pure compound was tested on the guinea pig uterus based on its ability to contract the relaxed uterus. The tissue was spiked with a standard oxytocic agent which induces contraction of the tissue. The efficacy of the testing agent was measured by its ability to contract the uterus by comparing the height of contraction with the standard oxytocin (Table 1). This example illustrates the procedure used for testing the crude extract and the detailed procedure followed.

TABLE 1

Oxytocic activity of the methanol extract against standard oxytocin

| Crude extract | 50 µg/ml | 250 µg/ml |
|---|---|---|
| Activity (%) | 13.3 | 126.3 |

EXAMPLE IV

The crude extract was fractionated into different fractions using solvents of increasing polarity such as petroleum ether, chloroform, n-butanol and the aqueous residue fraction. All four fractions were again subjected to the activity test. Although the first three fractions were found to be active, both at 50 and 250 µg/l concentration (Table 2), the chloroform fraction was chosen for follow-up studies. This example illustrates the activity tests with all 4 fractions of the crude methanol extract.

TABLE 2

Oxytocic activity of the fractions against standard oxytocin (%)

| Fractions | 50 µg/ml | 250 µg/ml |
|---|---|---|
| Petroleum ether | 57.4 | 102.5 |
| Chloroform | 47.1 | 104.6 |
| N-butanol | 83.8 | 100.0 |
| Aqueous | not active | not active |

EXAMPLE V

Figure 1:
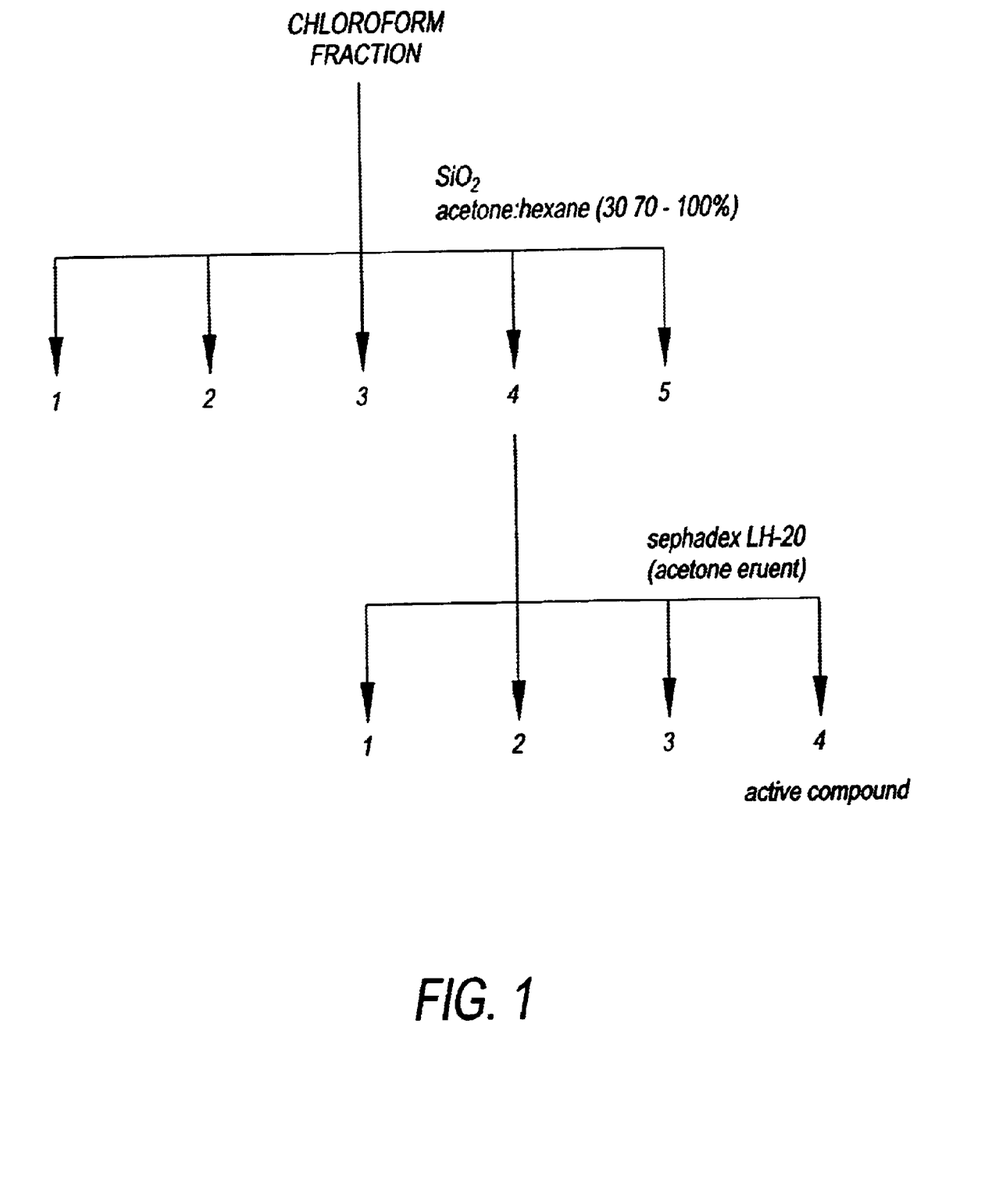
FIG. 1 represents the bioassay-guided fractionation followed for purification of the compound 2-deoxy ecdysterone from the crude chloroform fraction of the methanol extract of Zoanthus sp.
Figure 2:
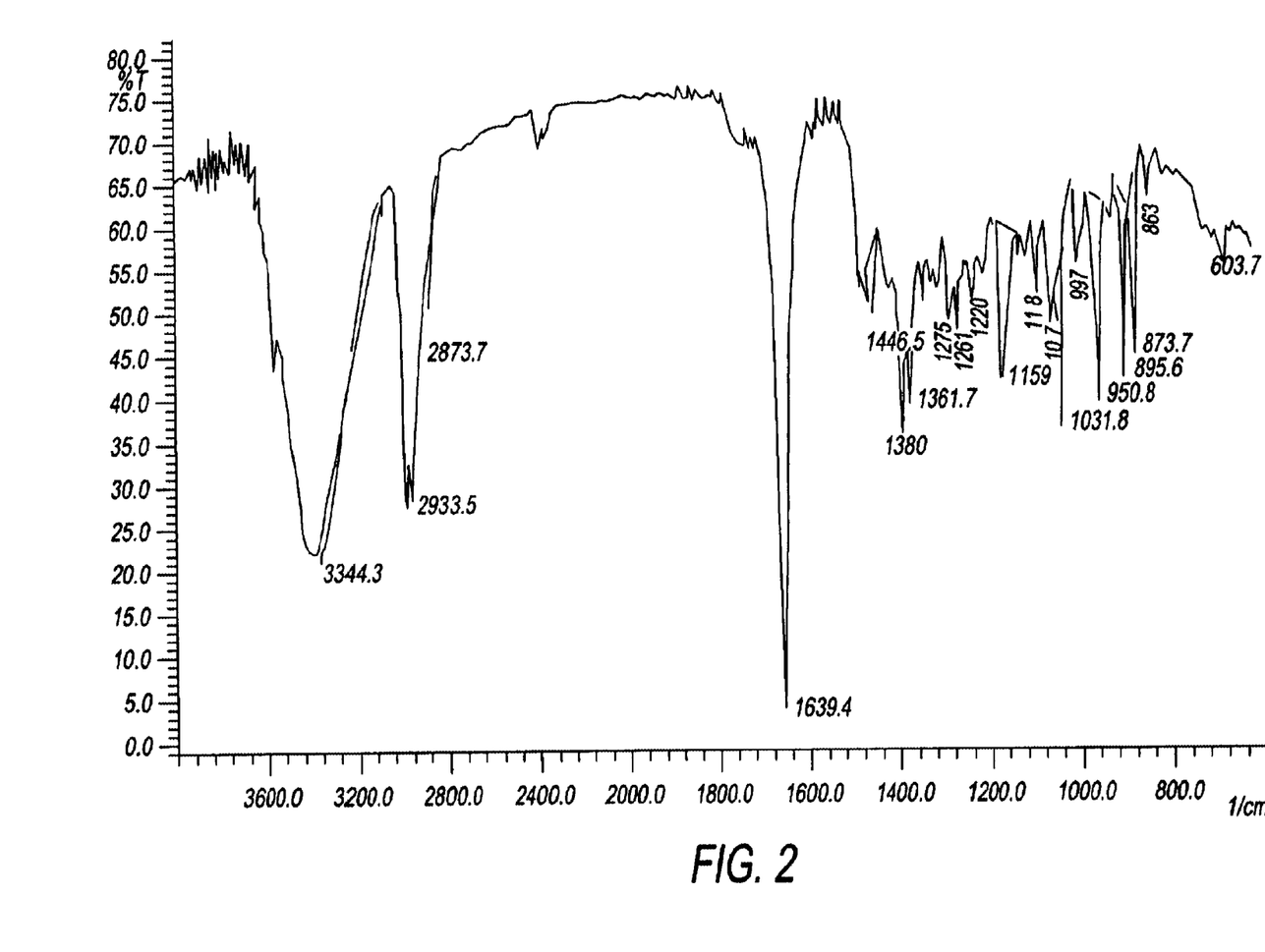
FIG. 2, represents the IR spectrum of the white solid isolated from the chloroform fraction of Zoanthus sp.
Figure 3:
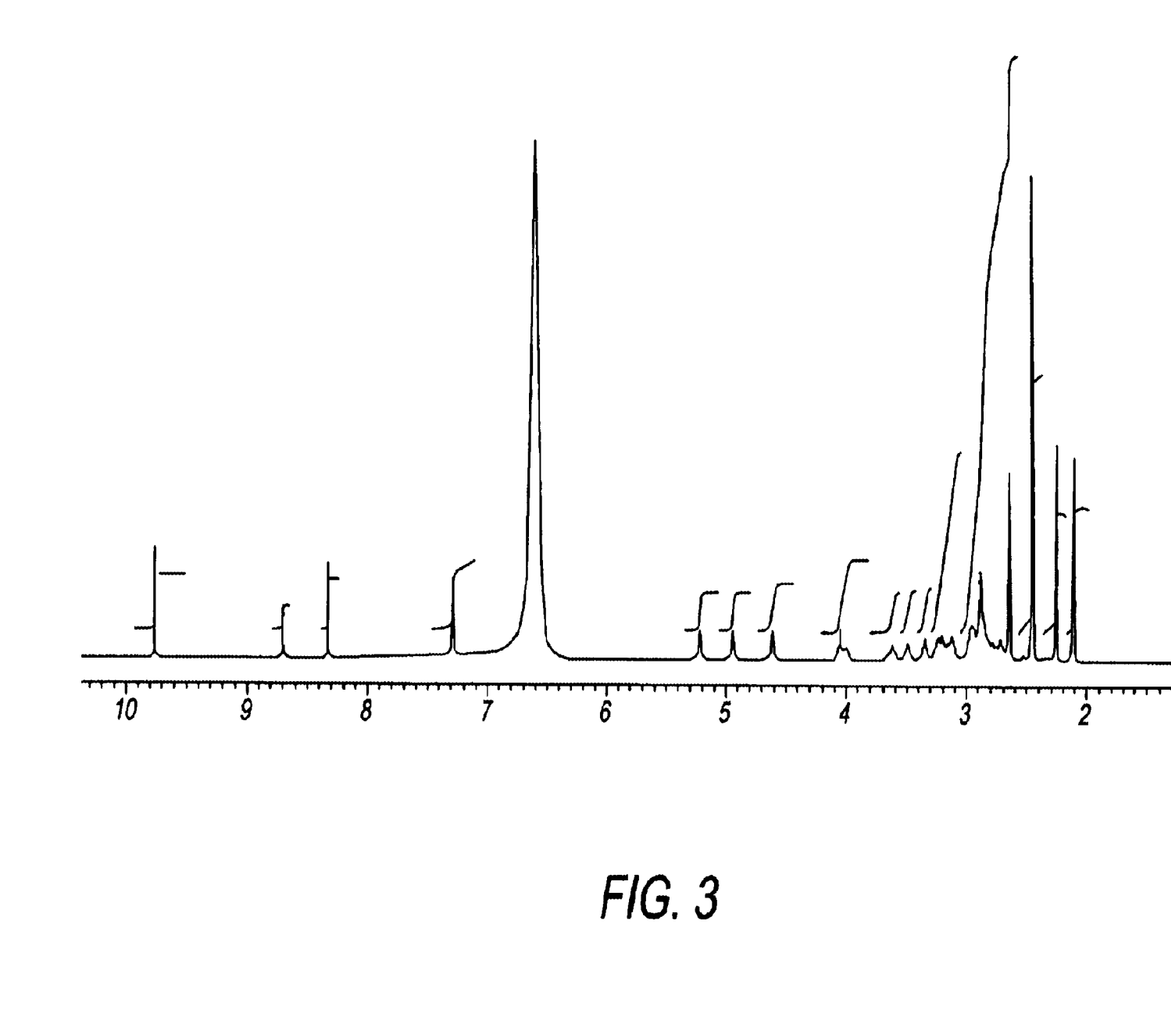
FIG. 3, represents the $^1H$ NMR spectrum of the compound indicating its structure as a polyhydroxy sterol derivative.
Figure 4:
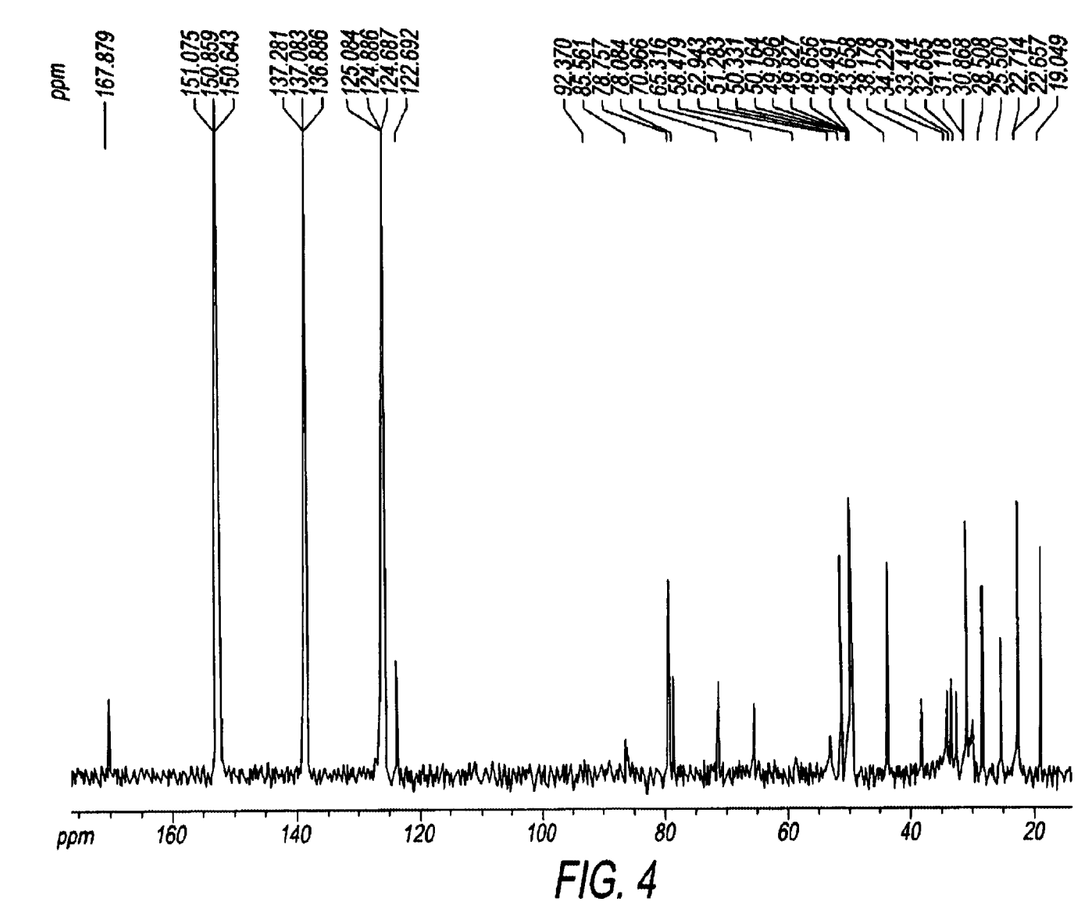
FIG. 4, represents the $^{13}C$ NMR spectrum of the compound indicating its structure as 2-deoxy ecdysterone.
Figure 5:
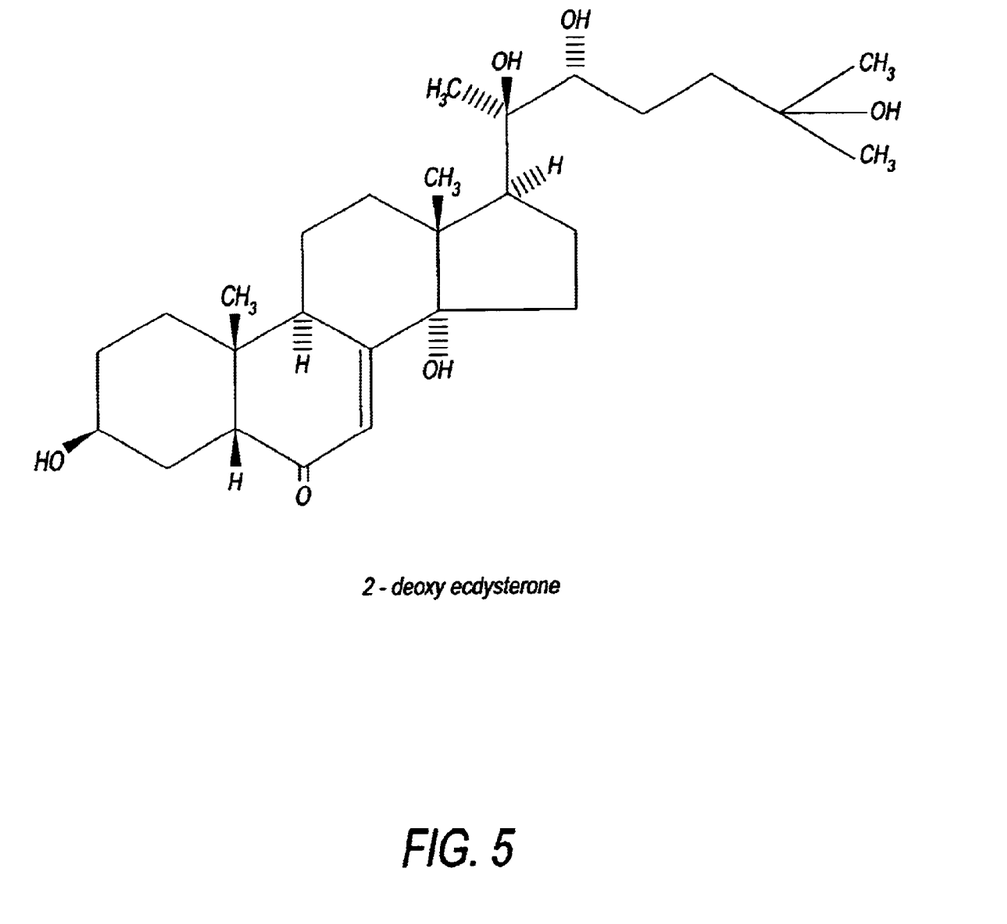
FIG. 5, represents the structure of the purified compound, 2-deoxy ecdysterone.
Figure 6:
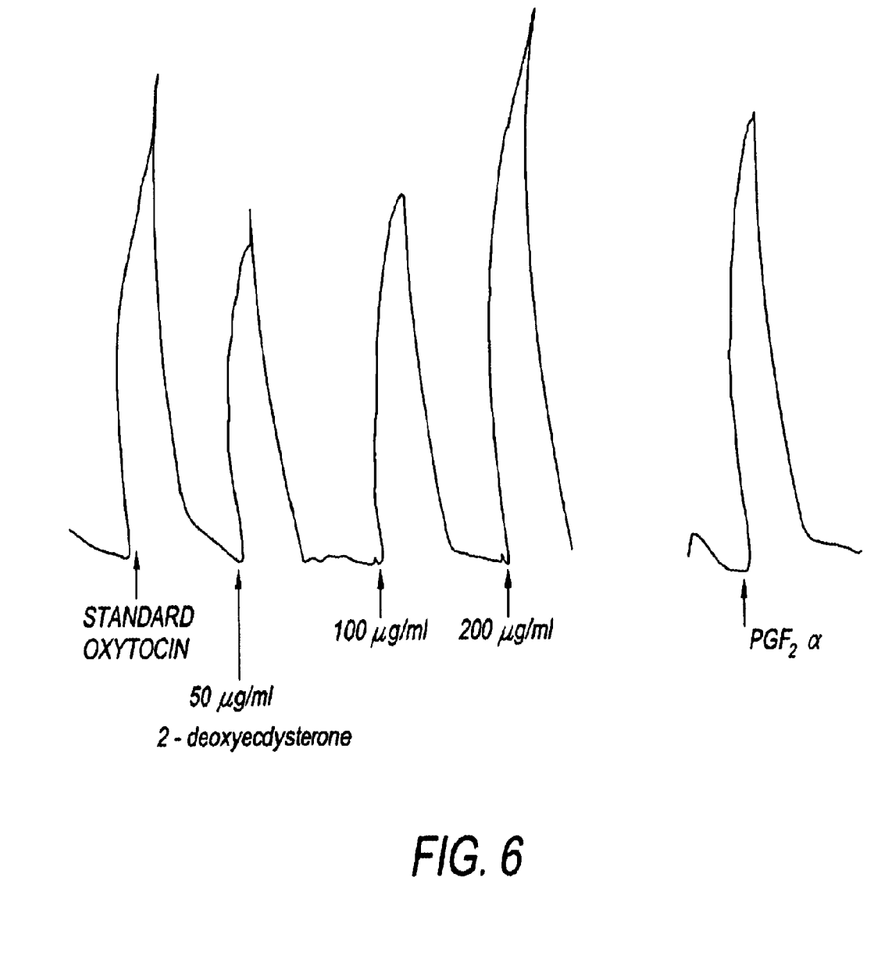
FIG. 6, represents the kymograph that was obtained during the testing of the compound for its oxytocic property on the isolated guinea-pig uterus.

The above chloroform fraction was purified by chromatography over silica gel (mesh 60–120, acetone-hexane gradient system) and sephadex LH-20 (acetone eluent) columns. This led to the isolation of the active compound as a white solid in pure form (50 mg, FIG. 1), $[\alpha]_D^{25}=75.11$, c=1.2, MeOH. The compound had an Rf value of 0.72 during TLC analysis ($SiO_2$, mobile phase-50% acetone:petroleum ether). IR spectrum showed peaks at 3350, 2933, 2874, 1649 and 1447 (FIG. 2). FABMS indicated molecular weight of this compound to be 464. The fragment ions at m/z 447$(M+H-H_2O)^+$, 429 $(M+H-2H_2O)^+$, 411$(M+H-3H_2O)$, were indicative of successive losses of elements of water. HRMS revealed its molecular formula to be $C_{27}H_{44}O_6$ (observed m/z 465.3229 as against the calculated value of 465.3216 for the $[M+H]^+$ ion). Comparison of the $^1H$ & $^{13}C$ NMR values (FIGS. 3 & 4) of the compound with those of ecdysone, ecdysterone and related compounds (Galbraith M N, Horn D H S, Middleton E J & Hackney R J, Structure of Deoxy ecdysterone, a second crustacean moulting hormone, Chem commun, 83,1968; Chong Y. K, Galbraith M N & Horn D H S, Isolation of Deoxycrustecdysone, Deoxyecdysone and (α-Ecdysone from the fern *Blechnum minus, Chem comm.* 1217,1970) revealed its structure to be 2-deoxy ecdysterone (FIG. 5). It was found that the percentage of active component oxytocin contained in 50 µg/ml of compound amounts to 80.8%, that at 100 µg/ml to 92.3% which further increases to 118.0% at concentration of 200 µg/ml (FIG. 6, Table 3). Uterine contractions produced by the compound were also compared with the standard contraction produced by prostaglandin ($PGF_2\alpha$). It was observed that for the active compound, the percentage of active component $PGF_{2\alpha}$ contained in 50 µg/ml of compound amounts to 69.4%, that at 100 µg/ml to 82.3% which further increases to 114.1% at concentration of 200 µg/ml (FIG. 6 and Table 3).

This example illustrates purification, identification, and oxytocic activity testing of the compound, 2-deoxy ecdysterone.

TABLE 3

Response of 2-deoxy ecdysterone compared to oxytocin and $PGF_{2\alpha}$

| Concentration | 50 µg/ml | 100 µg/ml | 200 µg/ml |
|---|---|---|---|
| % response compared to standard oxytocin | 80.8 | 92.3 | 118.0 |
| % response compared to standard $PGF_{2\alpha}$ | 69.4 | 82.3 | 114.1 |

What is claimed is:

1. A method of inducing uterus contractions in a mammal, comprising:
   administering to said mammal an effective amount of 2-deoxy ecdysterone prepared by a process comprising isolating and purifying 2-deoxy ecdysterone from Zoanthus sp. thereby inducing uterus contractions.

2. The method of claim 1, wherein said 2-deoxy ecdysterone is in an amount about 50 to about 200 µg/ml having activity from about 80% to about 118% when compared to standard oxytocin in a uterine contraction test.

3. The method of claim 1, wherein said 2-deoxy ecdysterone is in an amount about 50 to about 200 µg/ml having activity from about 69% to about 114% when compared to standard $PGF_{2\alpha}$ in a uterine contraction test.

4. The method of claim 1 wherein inducing uterus contractions induces labour.

5. The method of claim 1 wherein inducing uterus contractions augments labour.

6. The method of claim 1 wherein inducing uterus contractions is for controlling postpartum uterine atony.

7. The method of claim 1 wherein inducing uterus contractions is for controlling postpartum uterine hemorrhage.

8. The method of claim 1 wherein inducing uterus contractions is after a cesarean section.

9. The method of claim 1 wherein inducing uterus contractions is during uterine surgery.

10. The method of claim 1, wherein said isolating and purifying 2-deoxy ecdysterone comprises the steps of:
   (a) preparing crude methanol extract of Zoanthus sp.;
   (b) subjecting said crude methanol extract to fractionation using petroleum ether, chloroform, n-butanol or mixtures thereof to yield an active fraction;

(c) subjecting said active fraction to chromatography over silica gel to obtain partially purified active compound; and (d) subjecting the partially purified active compound obtained from step (c) above to gel permeation chromatography over hydroxproplylated cross-linked detra gel LH-20, thereby obtaining the active pure compound 2-deoxy ecdysterone.

11. The method of claim 10, wherein step (b) uses petroleum ether and the petroleum ether active fraction of Zoanthus sp exhibits oxytocic activity up to 57.4% and 102.5% at 50 $\mu$g/ml and 250 $\mu$g/ml dosage, respectively, as compared to standard oxytocin in a uterine contraction test.

12. The method of claim 10, wherein step (b) uses chloroform and the chloroform active fraction of Zoanthus sp exhibits oxytocic activity up to 47.1% and 104.6% at 50 $\mu$g/ml and 250 $\mu$g/ml dosage, respectively, as compared to standard oxytocin in a uterine contraction test.

13. The method of claim 10, wherein step (b) uses n-butanol and the n-butanol active fraction of Zoanthus sp exhibits oxytocic activity up to 83.8% and 100.0% at 50 $\mu$g/ml and 250 $\mu$g/ml dosage, respectively, as compared to standard oxytocin in a uterine contraction test.

\* \* \* \* \*